US007268223B2

(12) United States Patent
Renauld et al.

(10) Patent No.: US 7,268,223 B2
(45) Date of Patent: Sep. 11, 2007

(54) ISOLATED NUCLEIC ACID MOLECULES WHICH ENCODE A SOLUBLE IL-TIF RECEPTOR OR BINDING PROTEIN WHICH BINDS TO IL-TIF/IL-22, AND USES THEREOF

(75) Inventors: Jean-Christophe Renauld, Brussels (BE); Laure Dumoutier, Brussels (BE)

(73) Assignee: Wyeth, Collegeville, PA (US)

( * ) Notice: Subject to any disclaimer, the term of this patent is extended or adjusted under 35 U.S.C. 154(b) by 444 days.

(21) Appl. No.: 09/919,162

(22) Filed: Jul. 31, 2001

(65) Prior Publication Data

US 2004/0071699 A1 Apr. 15, 2004

Related U.S. Application Data

(60) Provisional application No. 60/245,495, filed on Nov. 3, 2000, provisional application No. 60/234,583, filed on Sep. 22, 2000.

(51) Int. Cl.
*C07H 21/04* (2006.01)
(52) U.S. Cl. ............... 536/23.5; 530/351; 435/69.1
(58) Field of Classification Search ............ 435/69.1, 435/320.1, 252.3, 325, 6; 536/23.5; 530/350, 530/351
See application file for complete search history.

(56) References Cited

U.S. PATENT DOCUMENTS

| 6,740,520 | B2 | 5/2004 | Goddard et al. | |
|---|---|---|---|---|
| 6,897,292 | B2 | 5/2005 | Presnell et al. | |
| 7,094,570 | B2 | 8/2006 | Renauld et al. | |
| 2002/0012669 | A1* | 1/2002 | Presnell et al. | 424/192.1 |
| 2003/0022827 | A1 | 1/2003 | Weiss et al. | |

FOREIGN PATENT DOCUMENTS

| EP | 11910357 | 8/2001 |
|---|---|---|
| WO | WO94/01548 | 1/1994 |
| WO | 98/02542 | 1/1998 |
| WO | 99/07848 | 2/1999 |
| WO | 99/61617 | 12/1999 |
| WO | 00/24578 | 5/2000 |
| WO | 00/55204 | 9/2000 |
| WO | 00/65027 | 11/2000 |
| WO | 00/73457 | 12/2000 |
| WO | 01/40467 | 1/2001 |
| WO | WO 01/36467 | 5/2001 |
| WO | 01/40467 | 6/2001 |
| WO | WO 01/46422 | 6/2001 |
| WO | WO 01/66740 | 9/2001 |
| WO | WO 01/98432 | 12/2001 |
| WO | 02/12345 | 2/2002 |
| WO | WO 02/24888 | 3/2002 |
| WO | WO 02/066647 | 8/2002 |
| WO | WO 02/077174 | 10/2002 |

OTHER PUBLICATIONS

Dumoutier, et al., "Cloning and Characterization of IL-22 Binding Protein, a Natural Antagonist of IL-10 Related T Cell-Derived Inducible Factor/IL-22," J. Immunol 766:7090-7095 (2001).
Gruenberg, et al., "A soluble homologue of the human IL-10 receptor with preferential expression in placenta," Genes & Immunity 2:329-334 (2001).
Kotenko, et al., "Identification of the Functional interleukin-22 (IL-22) Receptor Complex," J.Biol. Chem. 276(4):2725-2732 (2001).
Kotenko, et al., "Identification, Cloning and Characterization of a Novel Soluble Receptor That Binds IL-22 and Neutralizes Its Activity," J. Immunol 166:7096-7103 (2001).
Xu, et al., "A soluble Class II Cytokine Receptor, IL-22 RA2, is a Naturally Occurring IL-22 antagonist," Proc. Natl. Acad. Sci. USA 98(17):9511-9516 (2001).
Xie, et al., "Interleukin (IL-22), a Novel Human Cytokine That Signals Through the Interleukin Receptor-related proteins CRF2-4 and IL-22R." J. Biol. Chem 275(40):31335-31339 (2000).
Opal, et al., "Impact of Basic Research on Tomorrow's Medicine," CHEST 117:1162-1172 (2000).
Kotenko, et al., "Jak-Stat signal transduction pathway through the eyes of cytokine class II receptor complexes," Oncogene 19:2557-2565 (2000).
Dumoutier, et al., "Human interleukin-10 related T cell derived inducible factor: Molecular Cloning and Functional Characterization A An Hepatocyte Stimulating Factor," Proc. Natl. Acad. Sci. USA 97(18):10144-10149 (2000).
Fernandez-Botran, "Soluble Cytokine Receptors: Basic Immunology and Clinical Applications," Critical Reviews in Clinical Laboratory Sciences 36(3):165-224 (1999).
Kotenko, et al., "Identification and Functional Characterization of a Second Chain of the Interleukin-10 Receptor Complex," EMBO J 16(19):5894-5903 (1997).
Meagher, et al., "Assay For Measuring Soluble Cellular Adhesion Molecules and Soluble Cytokine Receptors," J. Immunol Meth. 191:97-112 (1996).
Heaney, et al., "Soluble Cytokine Receptors," Blood 87(3):847-857 (1996).
EMBL Online: Accession No. AL050337 (May 26, 1999).
Parrish-Novak, et al., "Interleukin-21 and its receptor are involved in NK cell expansion and regulation of lymphocyte function," Nature 408:57-63 (Nov. 2, 2000).
Xie, et al., "Interleukin (IL-22), a Novel Human Cytokine That Signals Through the Interleukin Receptor-related proteins CRF 2-4 and IL-22R." J. Biol. Chem 275 (40):51335-51339 (Oct. 6, 2000).

* cited by examiner

*Primary Examiner*—Lorraine Spector
*Assistant Examiner*—Dong Jiang
(74) *Attorney, Agent, or Firm*—Finnegan, Henderson, Farabow, Garrett & Dunner, LLP

(57) ABSTRACT

The invention relates to soluble proteins which bind to the molecule known as IL-TIF/IL-22. The proteins can antagonize the effect of IL-TIF/IL-22 on target cells. The nucleic acid molecules encoding the proteins, and uses of the protein, are also described.

2 Claims, No Drawings

SEQUENCE LISTING

```
<160> NUMBER OF SEQ ID NOS: 11

<210> SEQ ID NO 1
<211> LENGTH: 21
<212> TYPE: DNA
<213> ORGANISM: Homo sapiens

<400> SEQUENCE: 1
agggtacaat ttcagtcccg a                                              21

<210> SEQ ID NO 2
<211> LENGTH: 21
<212> TYPE: DNA
<213> ORGANISM: Homo sapiens

<400> SEQUENCE: 2
cggcgtcatg ctccattctg a                                              21

<210> SEQ ID NO 3
<211> LENGTH: 28
<212> TYPE: DNA
<213> ORGANISM: Homo sapiens

<400> SEQUENCE: 3
tgaacagtca cactcgagac catgatgc                                       28

<210> SEQ ID NO 4
<211> LENGTH: 25
<212> TYPE: DNA
<213> ORGANISM: Homo sapiens

<400> SEQUENCE: 4
catcctgttc tcgaggagct ttaga                                          25

<210> SEQ ID NO 5
<211> LENGTH: 2271
<212> TYPE: DNA
<213> ORGANISM: Homo sapiens

<400> SEQUENCE: 5
ctgccttaaa cccgggagtg attgtctgtt tgtggatttt acagtttcct ctttggtcct     60
gagctggtta aaaggaacac tggttgcctg aacagtcaca cttgcaacca tgatgcctaa   120
acattgcttt ctaggcttcc tcatcagttt cttccttact ggtgtagcag gaactcagtc   180
aacgcatgag tctctgaagc ctcagagggt acaatttcag tcccgaaatt ttcacaacat   240
tttgcaatgg cagcctggga gggcacttac tggcaacagc agtgtctatt ttgtgcagta   300
```

-continued

```
caaaatatat ggacagagac aatggaaaaa taaagaagac tgttggggta ctcaagaact      360
ctcttgtgac cttaccagtg aaacctcaga catacaggaa ccttattacg ggagggtgag      420
ggcggcctcg gctgggagct actcagaatg gagcatgacg ccgcggttca ctccctggtg      480
ggaaacaaaa atagatcctc cagtcatgaa ataacccaa gtcaatggct ctttgttggt       540
aattctccat gctccaaatt taccatatag ataccaaaag gaaaaaaatg tatctataga      600
agattactat gaactactat accgagtttt tataattaac aattcactag aaaaggagca      660
aaaggtttat gaaggggctc acagagcggt tgaaattgaa gctctaacac cacactccag      720
ctactgtgta gtggctgaaa tatatcagcc catgttagac agaagaagtc agagaagtga      780
agagagatgt gtggaaattc catgacttgt ggaatttggc attcagcaat gtggaaattc      840
taaagctccc tgagaacagg atgactcgtg tttgaaggat cttatttaaa attgtttttg      900
tattttctta aagcaatatt cactgttaca ccttggggac ttctttgttt atccattctt      960
ttatccttta tatttcattt gtaaactata tttgaacgac attcccccg aaaaattgaa      1020 atgtaaagat gaggcagaga ataagtgtt ctatgaaatt cagaacttta tttctgaatg       1080
taacatccct aataacaacc ttcattcttc taatacagca aaataaaaat ttaacaacca      1140
aggaatagta tttaagaaaa tgttgaaata atttttttaa aatagcatta cagactgagg      1200
cggtcctgaa gcaatggttt ttcactctct tattgagcca attaaattga cattgctttg      1260
acaatttaaa acttctataa aggtgaatat ttttcataca tttctatttt atatgaatat      1320 acttttttata tatttattat tattaaatat ttctacttaa tgaatcaaaa ttttgttta      1380 aagtctactt tatgtaaata agaacaggtt ttggggaaaa aaatcttatg atttctggat      1440
tgatatctga attaaaacta tcaacaacaa ggaagtctgc tctgtacaat tgtccctcat      1500
ttaaaagata tattaagctt ttcttttctg tttgtttttg ttttgtttag tttttaatcc      1560
tgtcttagaa gaacttatct ttattctcaa aattaaatgt aattttttta gtgacaaaga      1620
agaaaggaaa cctcattact caatccttct ggccaagagt gtcttgcttg tggcgccttc      1680
ctcatctcta tataggagga tcccatgaat gatggtttat tgggaactgc tggggtcgac      1740
cccatacaga gaactcagct tgaagctgga agcacacagt gggtagcagg agaaggaccg      1800
gtgttggtag gtgcctacag agactataga gctagacaaa gccctccaaa ctggccctc      1860 ctgctcactg cctctcctga gtagaaatct ggtgacctaa ggctcagtgt ggtcaacaga      1920
aagctgcctt cttcacttga ggctaagtct tcatatatgt ttaaggttgt ctttctagtg      1980
aggagataca tatcagagaa catttgtaca attccccatg aaaattgctc caaagttgat      2040
aacaatatag tcggtgcttc tagttatatg caagtactca gtgataaatg gattaaaaaa      2100
tattcagaaa tgtattgggg ggtggaggag aataagaggc agagcaagag ctagagaatt      2160
ggtttccttg cttccctgta tgctcagaaa acattgattt gagcatagac gcagagactg      2220
aaaaaaaaat ttactttgat ctctgttttt gaattcttat tatttatatt t               2271
```

<210> SEQ ID NO 6
<211> LENGTH: 231
<212> TYPE: PRT
<213> ORGANISM: Homo sapiens

<400> SEQUENCE: 6

```
Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
            20                  25                  30
```

```
Arg Val Gln Phe Gln Ser Arg Asn Phe His Asn Ile Leu Gln Trp Gln
            35                  40                  45

Pro Gly Arg Ala Leu Thr Gly Asn Ser Ser Val Tyr Phe Val Gln Tyr
 50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Thr Ser Asp Ile Gln
                 85                  90                  95

Glu Pro Tyr Tyr Gly Arg Val Arg Ala Ala Ser Ala Gly Ser Tyr Ser
                100                 105                 110

Glu Trp Ser Met Thr Pro Arg Phe Thr Pro Trp Glu Thr Lys Ile
            115                 120                 125

Asp Pro Pro Val Met Asn Ile Thr Gln Val Asn Gly Ser Leu Leu Val
            130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
            210                 215                 220

Glu Arg Cys Val Glu Ile Pro
225                 230

<210> SEQ ID NO 7
<211> LENGTH: 37
<212> TYPE: DNA
<213> ORGANISM: Homo sapiens

<400> SEQUENCE: 7
ccaacttcca tgatcaatgg aatttccaca catctct                       37

<210> SEQ ID NO 8
<211> LENGTH: 33
<212> TYPE: DNA
<213> ORGANISM: Homo sapiens

<400> SEQUENCE: 8
aagactgagt tgatcaagag aatcgagcct aga                           33

<210> SEQ ID NO 9
<211> LENGTH: 27
<212> TYPE: DNA
<213> ORGANISM: Homo sapiens

<400> SEQUENCE: 9
aatgtctaga tgctgttctc atttacc                                  27

<210> SEQ ID NO 10
<211> LENGTH: 2367
<212> TYPE: DNA
<213> ORGANISM: Homo sapiens

<400> SEQUENCE: 10
ctgccttaaa cccgggagtg attgtctgtt tgtggatttt acagtttcct ctttggtcct  60
```

-continued

```
gagctggtta aaaggaacac tggttgcctg aacagtcaca cttgcaacca tgatgcctaa    120
acattgcttt ctaggcttcc tcatcagttt cttccttact ggtgtagcag gaactcagtc    180
aacgcatgag tctctgaagc ctcagagggt acaatttcag tcccgaaatt ttcacaacat    240
tttgcaatgg cagcctggga gggcacttac tggcaacagc agtgtctatt ttgtgcagta    300
caaaatcatg ttctcatgca gcatgaaaag ctctcaccag agccaagtgg atgcttggca    360
gcacatttct tgtaacttcc caggctgcag aacattggct aaatatggac agagacaatg    420
gaaaaataaa gaagactgtt ggggtactca agaactctct tgtgaccttc ccagtgaaac    480
ctcagacata caggaacctt attacgggag ggtgagggcg gcctcggctg ggagctactc    540
agaatggagc atgacgccgc ggttcactcc ctggtgggaa acaaaaatag atcctccagt    600
catgaatata acccaagtca atggctcttt gttggtaatt ctccatgctc caaatttacc    660
atatagatac caaaaggaaa aaatgtatc tatagaagat tactatgaac tactataccg     720 agttttata attaacaatt cactagaaaa ggagcaaaag gtttatgaag gggctcacag     780
agcggttgaa attgaagctc taacaccaca ctccagctac tgtgtagtgg ctgaaatata    840
tcagcccatg ttagacagaa gaagtcagag aagtgaagag agatgtgtgg aaattccatg    900
acttgtggaa tttggcattc agcaatgtgg aaattctaaa gctccctgag aacaggatga    960
ctcgtgtttg aaggatctta tttaaaattg ttttttgtat ttcttaaagc aatattcact   1020
gttacacctt ggggacttct ttgtttatcc attcttttat cctttatatt tcatttgtaa   1080
actatatttg aacgacattc cccccgaaaa attgaaatgt aaagatgagg cagagaataa   1140
agtgttctat gaaattcaga actttatttc tgaatgtaac atccctaata acaaccttca   1200 ttcttcaat acagcaaaat aaaaatttaa caaccaagga atagtattta agaaaatgtt    1260
gaaataattt ttttaaaata gcattacaga ctgaggcggt cctgaagcaa tggttttca    1320 ctctcttatt gagccaatta aattgacatt gctttgacaa tttaaaactt ctataaaggt   1380 gaatatttt catacatttc tattttatat gaatatactt tttatatatt tattattatt    1440
aaatatttct acttaatgaa tcaaaatttt gttttaaagt ctactttatg taaataagaa   1500
caggttttgg ggaaaaaaat cttatgattt ctggattgat atctgaatta aaactatcaa   1560
caacaaggaa gtctgctctg tacaattgtc cctcatttaa aagatatatt aagcttttct   1620
tttctgtttg ttttttgtttt gtttagtttt taatcctgtc ttagaagaac ttatctttat   1680
tctcaaaatt aaatgtaatt ttttttagtga caaagaagaa aggaaacctc attactcaat   1740
ccttctggcc aagagtgtct tgcttgtggc gccttcctca tctctatata ggaggatccc   1800
atgaatgatg gtttattggg aactgctggg gtcgacccca tacagagaac tcagcttgaa   1860
gctggaagca cacagtgggt agcaggagaa ggaccggtgt tggtaggtgc ctacagagac   1920
tatagagcta gacaaagccc tccaaactgg cccctcctgc tcactgcctc tcctgagtag   1980
aaatctggtg acctaaggct cagtgtggtc aacagaaagc tgccttcttc acttgaggct   2040
aagtcttcat atatgtttaa ggttgtcttt ctagtgagga gatacatatc agagaacatt   2100
tgtacaattc cccatgaaaa ttgctccaaa gttgataaca atatagtcgg tgcttctagt   2160
tatatgcaag tactcagtga taaatggatt aaaaaatatt cagaaatgta ttgggggtg    2220 gaggagaata agaggcagag caagagctag agaattggtt tccttgcttc cctgtatgct   2280
cagaaaacat tgatttgagc atagacgcag agactgaaaa aaaaatttac tttgatctct   2340 gttttttgaat tcttattatt tatatttt                                     2367
```

```
<210> SEQ ID NO 11
<211> LENGTH: 263
<212> TYPE: PRT
<213> ORGANISM: Homo sapiens

<400> SEQUENCE: 11

Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
                35                  40                  45

Pro Gly Arg Ala Leu Thr Gly Asn Ser Ser Val Tyr Phe Val Gln Tyr
        50                  55                  60

Lys Ile Met Phe Ser Cys Ser Met Lys Ser Ser His Gln Ser Gln Val
65                  70                  75                  80

Asp Ala Trp Gln His Ile Ser Cys Asn Phe Pro Gly Cys Arg Thr Leu
                85                  90                  95

Ala Lys Tyr Gly Gln Arg Gln Trp Lys Asn Lys Glu Asp Cys Trp Gly
            100                 105                 110

Thr Gln Glu Leu Ser Cys Asp Leu Thr Ser Glu Thr Ser Asp Ile Gln
            115                 120                 125

Glu Pro Tyr Tyr Gly Arg Val Arg Ala Ala Ser Ala Gly Ser Tyr Ser
        130                 135                 140

Glu Trp Ser Met Thr Pro Arg Phe Thr Pro Trp Trp Glu Thr Lys Ile
145                 150                 155                 160

Asp Pro Pro Val Met Asn Ile Thr Gln Val Asn Gly Ser Leu Leu Val
                165                 170                 175

Ile Leu His Ala Pro Asn Leu Pro Tyr Arg Tyr Gln Lys Glu Lys Asn
            180                 185                 190

Val Ser Ile Glu Asp Tyr Tyr Glu Leu Leu Tyr Arg Val Phe Ile Ile
            195                 200                 205

Asn Asn Ser Leu Glu Lys Glu Gln Lys Val Tyr Glu Gly Ala His Arg
        210                 215                 220

Ala Val Glu Ile Glu Ala Leu Thr Pro His Ser Ser Tyr Cys Val Val
225                 230                 235                 240

Ala Glu Ile Tyr Gln Pro Met Leu Asp Arg Arg Ser Gln Arg Ser Glu
                245                 250                 255

Glu Arg Cys Val Glu Ile Pro
            260
```

ISOLATED NUCLEIC ACID MOLECULES WHICH ENCODE A SOLUBLE IL-TIF RECEPTOR OR BINDING PROTEIN WHICH BINDS TO IL-TIF/IL-22, AND USES THEREOF

RELATED APPLICATIONS

This application claims priority of provisional applications 60/245,495 filed Nov. 3, 2000, and, 60/234,583 filed Sep. 22, 2000, both of which are incorporated by reference in their entirety.

FIELD OF THE INVENTION

This invention relates to newly isolated nucleic acid molecules, proteins and their uses. More specifically, it relates to a soluble protein which binds to the molecule referred to as IL-TIF/IL-22 or as it will be referred to hereafter "IL-22BP" or "IL-22 binding protein." The proteins of the invention inhibit TIF/IL-22 by binding thereto, and inhibiting IL-TIF/IL-22's effect on cells.

BACKGROUND AND PRIOR ART

The last decade has seen knowledge of the immune system and its regulation expand tremendously. One area of particular interest has been that of research on the proteins and glycoproteins which regulate the immune system. One of the best known families of these molecules are the cytokines. These are molecules which are involved in the "communication" of cells with each other. The individual members of the cytokine family have been found to be involved in a wide variety of pathological conditions, such as cancer and allergies. Whereas sometimes the cytokines are involved in the pathology of the condition, they are also known as being therapeutically useful.

Interleukins are one type of cytokine. The literature on interleukins is vast. An exemplary, but by no means exhaustive listing of the patents in this area includes U.S. Pat. No. 4,778,879 to Mertelsmann et al.; U.S. Pat. No. 4,490,289 to Stern; U.S. Pat. No. 4,518,584 to Mark et al.; and U.S. Pat. No. 4,851,512 to Miyaji et al., all of which involve interleukin-2 or "IL-2." Additional patents have issued which relate to interleukin-1 ("IL-1"), such as U.S. Pat. No. 4,808,611 to Cosman. The disclosure of all of these patents are incorporated by reference herein. More recent patents on different interleukins include U.S. Pat. No. 5,694,234 (IL-13); U.S. Pat. No. 5,650,492 (IL-12); U.S. Pat. Nos. 5,700,664, 5,371,193 and 5,215,895 (IL-11); U.S. Pat. Nos. 5,728,377, 5,710,251, 5,328,989 (IL-10); U.S. Pat. Nos. 5,580,753, 5,587,302, 5,157,112, 5,208,218 (IL-9); U.S. Pat. Nos. 5,194,375, 4,965,195 (IL-7); U.S. Pat. Nos. 5,723,120, 5,178,856 (IL-6), and U.S. Pat. No. 5,017,691 (IL-4). Even a cursory review of this patent literature shows the diversity of the properties of the members of the interleukin family. One can assume that the larger cytokine family shows even more diversity. See, e.g., Aggarwal et al., ed., Human Cytokines: Handbook For Basic And Clinical Research (Blackwell Scientific Publications, 1992), Paul, ed., Fundamental Immunology (Raven Press, 1993), pg 763-836, "T-Cell Derived Cytokines And Their Receptors", and "Proinflammatory Cytokines and Immunity," and Thomson, ed. "The Cytokine Handbook" (1998, Academic Press). All cited references are incorporated by reference.

The relationships between various cytokines are complex. As will be seen from the references cited herein, as the level of a particular cytokine increases or decreases, this can affect the levels of other molecules produced by a subject, either directly or indirectly. Among the affected molecules are other cytokines.

The lymphokine IL-9, previously referred to as "P40," is a T-cell derived molecule which was originally identified as a factor which sustained permanent antigen independent growth of T4 cell lines. See, e.g., Uyttenhove et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed on restricted T4 cell lines, failing to show activity on CTLs or freshly isolated T cells. See, e.g., Uyttenhove et al., supra, and Schmitt et al., Eur. J. Immunol. 19: 2167 (1989). This range of activity was expanded when experiments showed that IL-9 and the molecule referred to as T cell growth Factor III ("TCGF III") are identical to MEA (Mast Cell Growth Enhancing Activity), a factor which potentiates the proliferative response of bone marrow derived mast cells to IL-3, as is described by Hültner et al., Eur. J. Immunol. 19: 2167 (1989) and in U.S. Pat. No. 5,164,317, the disclosures of both being incorporated by reference herein. It was also found that the human form of IL-9 stimulates proliferation of megakaryoblastic leukemia. See Yang et al., Blood 74: 1880 (1989). Recent work on IL-9 has shown that it also supports erythroid colony formation (Donahue et al., Blood 75(12): 2271-2275 (6-1990)); promotes the proliferation of myeloid erythroid burst formation (Williams et al., Blood 76: 306-311 (1990)); and supports clonal maturation of BFU-E's of adult and fetal origin (Holbrook et al., Blood 77(10): 2129-2134 (1991)). Expression of IL-9 has also been implicated in Hodgkins's disease and large cell anaplastic lymphoma (Merz et al., Blood 78(8): 1311-1317 (1990)). Genetic analyses of mice that were susceptible or resistant to the development of bronchial hyperresponsiveness have unraveled a linkage with the IL-9 gene as well as a correlation between IL-9 production and susceptibility in this model (Nicolaides et al., Proc. Natl. Acad. Sci. USA, 94, 13175-13180, (1997)). Human genetic studies also point to the IL-9 and IL-9R or "IL-9 receptor" genes as candidates for asthma therapy (Doull et al., Am. J. Respir. Crit. Care Med., 153, 1280-1284, (1996); Holroyd et al., Genomics 52, 233-235, (1998)). IL-9 transgenic mice allowed for the demonstration that increased IL-9 expression results in lung mastocytosis, hypereosinophilia, bronchial hyperresponsiveness and high levels of IgE (Temann et al., J. Exp. Med. 188, 1307-1320 (1998); Godfraind et al., J. Immunol. 160, 3989-3996 (1998); McLane et al., Am. J. Resp. Cell. Mol. 19:713-720 (1999)). Taken together, these observations strongly suggest that IL-9 plays a major role in this disease Additional work has implicated IL-9 and muteins of this cytokine in asthma and allergies. See, e.g. PCT Application US96/12757 (Levitt, et al), and PCT US97/21992 (Levitt, et al), both of which are incorporated by reference.

IL-9 is known to affect the levels of other molecules in subjects. See Louahed et al., J. Immunol. 154: 5061-5070 (1995), Demoulin et al., Mol. Cell. Biol. 16: 4710-4716 (1996), both incorporated by reference. It will be recognized that the molecules affected have their own functions in biological systems. For example, Demoulin et al. show that many of the known activities of IL-9 are mediated by activation of STAT transcription factors. As such, there is continued interest in trying to identify molecules whose presence and/or level is affected by other molecules, such as signal transduction molecules and cytokines.

A new member of the interleukin family is described in, e.g., U.S. patent application Ser. No. 09/419,568, filed Oct. 18, 1999, and incorporated by reference in its entirety. Also see Dumoutier, et al, "Human interleukin-10 related T cell derived inducible factor molecular cloning and function characterization as a hepatocyte stimulating factor," Proc. Natl. Acad. Sci. USA 97(18): 10144-10149 (2000), also incorporated by reference. Also see Dumoutier, et al, J. Immunol 164:1814 (2000), and Dumoutier, et al, Genes Immunol 1:488 (2000), both of which are incorporated by reference. Also see Ser. No. 09/626, 627 filed Jul. 27, 2000, incorporated by reference. Dumoutier, et al, Proc. Natl. Acad. Sci. 97(18): 10144-10149 (2000) also suggest that this new molecule, IL-TIF/IL-22, induces acute phase reactant production by liver cells, in vitro, and in vivo.

Xie, et al, J. Biol. Chem 27:31335-31339 (2000), have suggested that this molecule be renamed as IL-22. Xie et al also teach that the receptor for this molecule consists of two chains, each of which bind to the molecule. These chains are referred to as "CRF 2-4" and "CRF 2-9." The former is also referred to as "IL-10RB" because it is required for IL-10 signalling. See, e.g., Kotenko, et al, EMBO J. 16:5894 (1997).

The second chain, CRF 2-9, was originally considered to be an orphan receptor. This chain is also known as "ZCY-TOR 11," but Xie, et al., supra, have proposed it be renamed "IL-22R". Due to their structure, both chains are considered to belong to the class II cytokine receptor family (Kotenko, et al, Oncogene 19:2557 (2000)), which consists of 8 members of known function (i.e., two pairs of two receptor subunits for type I interferons (IFN-α, IFN-β, IFN-w, IFN-t) and type II (IFN-γ) interferon, IL-10R, tissue factor, and the two chains referred to supra. At least one orphan receptor, referred to as "CRF 2-8," is also a member of the family. These receptors are related by their extracellular domains, which have tandem fibronectin type III (FNIII) domains. Four of the genes encoding these proteins, i.e., "IFNAR1," "IFNAR2," "IIL10R2" and "IFNGR2," are located on human chromosome 21. The IFNGR1 and CRF2-8 genes map to chromosome 6, IL-22R is located on chromosome 1, and IL-10R1 is on chromosome 11.

Additional work on these molecules can be found in, e.g., International Patent Application Number PCT/US00/11479 (Publication Number WO 00/65027) and International Parent Application Number PCT/US99/11644 (Publication Number WO 99/61667). Also see Internation Patent Application Number PCT/US00/32703, publication number WO/01/40467, describing "ZCYTOR16."

A nucleic acid molecule has now been identified, and is referred to as IL-22 binding protein (IL-22BP), which encodes another molecule which binds IL-TIF/IL-22. The protein which the nucleic acid molecule encodes serves to inhibit the effect that IL-TIF/IL-22 has on target cells. Further, a second form of the nucleic acid molecule has been identified as a splice variant of the first. This second molecule contains an additional 96 nucleotides, and encodes an additional 32 amino acids.

These, as well as other features of the invention, will be seen in the disclosure which follows.

DETAILED DESCRIPTION OF PREFERRED EMBODIMENTS

EXAMPLE 1

This example describes experiments which were carried out to identify potential new members of the class II cytokine receptor family. Receptors for the interferons, and for IL-10, are members of this family.

The amino acid sequence of the extracellular domain of human IL-10R was used to screen the database of the Sanger Center, using TBLASTN software.

Two short regions of homology were identified in a BAC clone from chromosome 6q24 (Genbank Accession Number AL 05337), about 40 kilobases from the known IFNGR-1 gene.

The first fragment showed 40% amino acid identity with residues 63-119 of IL-10R, while the other, located 3 kb upstream, showed 47% identity with residues 29-47.

Once the BAC sequence was identified, it was analyzed further, using the NIX analysis program The software predicted a gene comprising 5 exons, stretching over about 16 kilobases, with the last exon corresponding to several EST sequences.

EXAMPLE 2

These experiments were designed to determine the pattern of tissue distribution of the molecule identified in example 1, supra.

Total RNA was isolated from samples taken from various organs using guanidium isothiocyanate lysis and CsCl gradient centrifugation, following Ausubel, et al., *Current Protocols In Molecular Biology* (1993), incorporated by reference. Samples of RNA (5 ug), were reverse transcribed with an oligo(dT) primer, and the resulting cDNA was amplified via PCR. Specifically, samples corresponding to 5 ng of total RNA were amplified using agggtacaat ttcagtcccg a (sense, SEQ ID NO: 1)

and cggcgtcatg ctccattctg a (antisense, SEQ ID NO: 2). The annealing temperature was 55° C. Resulting PCR products were analyzed in ethidium bromide stained, 1% agarose gels.

Strongest expression was found in breast tissue, and a clear signal was also detected in lungs and the intestinal tract (i.e., stomach and colon). Skin, testis, brain, heart, and thymus tissue were also positive, at lower levels, and not in all samples tested. There was no detectable expression in prostate, bladder, kidney, ovary, muscle, bone marrow, liver or uterine tissue.

One noteworthy feature of these results was the identification of a second band in some tissue samples, such as skin and lungs. The significance of this second band is discussed infra.

EXAMPLE 3

These experiments describe work in amplifying full length cDNA for the materials described supra.

Breast tissue RNA was prepared, as described supra, and was amplified via RT-PCR, as described supra, using:

```
                         (sense; SEQ ID NO: 3)
    tgaacagtca cactcgagac catgatgc,
and
                         (antisense; SEQ ID NO: 4)
    catcctgttc tcgaggagct ttaga.
```

These primers contain mutations which introduce an XhoI site to permit direct cloning into the pCEP4 plasmid described infra. A cDNA molecule was identified which consisted of 775 nucleotides, of which 693 constituted an open reading frame that encoded a protein of 231 amino acids, with a calculated molecular weight of about 27 kd. The nucleotide sequence, and the predicted amino acid sequence, are presented as SEQ ID NOS: 5 and 6.

Analysis of the predicted protein reveals a stretch of hydrophobic amino acids at the N-terminus, compatible with a signal peptide. There was significant homology to the extracellular domains of members of the IL-10 receptor family; however, the molecule under consideration lacked a hydrophobic transmembrane domain, suggesting it is a secreted protein.

When the deduced amino acid sequence was aligned with other proteins, 33% amino acid identity with the extracellular domain of IL-22R was found, as was 34% with orphan receptor CRF 2-8. Lower sequence identity was found with IL-10R (29%), CRF2-4/IL-10Rβ (30%), tissue factor (26%) and the four interferon receptor chains (23-25%). The predicted mature form of the protein contains 4 cysteine residues. These are conserved in most members of the class II cytokine receptors. Additionally, the structure of the gene, as deduced from the information presented herein, is of one that contains 5 exons, the first of which encodes the signal peptide, and the following four of which encode the mature protein.

EXAMPLE 4

The data developed supra showed that the molecule of interest had highest homology to the extracellular domain of IL-22R. Experiments were therefore designed to determine if the molecule bound to IL-TIF/IL-22.

A series of IL-22BP fusion proteins were made. The first, referred to as "IL-TIFR-Ig," was produced by first amplifying the full length open reading frame of the IL-22BP molecule referred to supra, using the following, mutated antisense primer:

ccaacttcca tgatcaatgg aatttccaca catctct (SEQ ID NO. 7)

This primer serves to introduce a BclI site into the stop codon of the ORF. In addition, a region comprising the hinge, CH2 and CH3 domains of murine IgG3 isotype heavy chain was amplified, using the known IgG3 anti-TNP hybridoma C3110. The following primers were used:

```
                     (sense, SEQ ID NO. 8)
    aagactgagt tgatcaagag aatcgagcct aga
    and (antisense, SEQ ID NO. 9)
    aatgtctaga tgctgttctc atttacc
```

These primers also contain BclI and XbaI sites for cloning.

Following amplification, both PCR products were digested, and cloned into pCEP4 plasmid, under control of CMV promoter, as described supra.

Clones were sequenced, using standard methodologies. These were then used to transfect HEK293 cells transiently, also as described supra. In brief, cells were seeded in 6 well plates, at $3\times10^5$ cells/well, one day prior to transfection. Standard, lipofectamine methodologies were used, using 2 ug of plasmid DNA. After transfection, cells were incubated in 1.5 ml of normal medium for 3 days.

In similar fashion, a fusion protein of IL-22R and the IgG3 Fc fragment was generated, known as IL-22R-Ig. These two fusion proteins were used together with a control fusion protein, i.e. IL-9-Ig, which had been made previously.

Assays were then carried out by coating polystyrene plates with either 0.083 mg/ml of recombinant human IL-TIF/IL-22, or 0.2 mg/ul bovine serum albumin, in 20 mm Tris and glycine buffer containing 30 mm NaCl, pH 9.2, overnight, at 4° C. Following washing in PBS buffer plus Tween 20 ($10^{-4}$) plates were blocked with PBS plus 1% BSA for two hours, and then 50 μl of supernatant from transiently transfected HEK293 cells was added. Plates were then incubated for 2 hours, at 37° C. Any bound fusion protein was detected, using murine anti-Ig polyclonal antibodies coupled to peroxidase. Detection was carried out using the peroxidase substrate "TMB", or (3,3',5,5'-tetramethylbenzidine), and stopped by 20 μl $H_2SO_4$.

The results indicated that IL-22BP-Ig and IL-22R-Ig both bind to IL-TIF/IL-22, but not bovine serum albumin. Supernatants of mock transfected cells, or IL-9-Ig did not detectably bind IL-TIF/IL-22.

EXAMPLE 5

These experiments describe studies designed to assess whether the protein of the invention was able to block IL-TIF/IL-22 activity.

To test this, the cell lines H4IIE and HT-29, referred to supra, were used. It is known that H41IE responds to IL-TIF/IL-22 by activation of STAT transcription factors, and acute phase reactant production. The HT-29 cell line shows STAT-3 activation. STAT activation by IL-TIF/IL-22 can be measured, in both cell lines, via the use of a luciferase reporter construct which includes 5 STAT binding sites, plus a minimal TK promoter. See Dumoutier, et al; Proc. Natl. Acad. Sci. USA, 97:10144 (2000), incorporated by reference.

The construct "pGRR5" was used. This construct contains 5 copies of the STAT binding site of the FcγR1 gene, upstream of a luciferase gene under control of a tk promoter. As an internal control, the vector pRL-TK was used. This construct contains the renilla luciferase gene under the control of the tk promoter.

The H4IIE and HT-29 cells were electroporated with 15 μg of pGRR5 and 1 μg pRL-TK (250V, 192Ω, 1,200 μF), and were then seeded at $4\times10^5$ cells/well. RAW 264.7 cells were transfected in the same way, the only difference being the resistance used (74Ω). This cell line was used to determine the effect of the IL-22BP on IL-10.

The transfected H4IIE or HT-29 cells were then stimulated with a preincubated (1 hour) mixture of recombinantly produced IL-TIF/IL-22, at varying concentrations and 5% supernatant (from HEK293 cells that had been transfected with the cDNA described herein), or a preincubated mixture of the IL-TIF and 5% supernatant from mock transfected cells. After two hours, luciferase activity was measured either in pelleted or lysed cells, or directly in plated cells, using a commercially available assay.

The results indicated that the STAT-activating activity of IL-TIF/IL-22 (at 4 ng/ml), was blocked completely when combined with supernatants from cells transfected by constructs encoding the IL-22BP protein or fusion proteins, described supra. This was the case for both H4IIE and HT-29 cells. In contrast, when IL-6 was used in place of IL-TIF/IL-22, there was no effect. Nor was IL-10 activity affected by pre-incubation with IL-IL-22BP protein or fusion protein.

EXAMPLE 6

Novick, et al, Cytokine 4:6 (1992), have shown that soluble IL-6 receptor can increase the sensitivity of cells to subliminal concentrations of its ligand. Studies were therefore carried out, in parallel to those presented spra, testing low (<25 ng/ml), and high (50-200 ng/ml) concentrations of IL-TIF/IL-22 in H4IIE cells. It was found that, at the low concentrations, STAT activation was blocked completely by IL-22BP but IL-22BP failed to block STAT activation in H4IIE cells, when high concentrations of IL-TIF were used. Decreasing the concentration of IL-22BP led to a loss of inhibitory effect, but did not reveal any potentiating activity for IL-TIF/IL-22.

EXAMPLE 7

Femandez-Botran, et al, J. Exp. Med 174:673 (1991) have shown that the soluble and transmembrane forms of the IL-4 receptor have similar association rates, but the soluble form has a higher dissociation rate. This indicates that the complexes formed by IL-4 and the IL-4 binding protein ("IL-4BP") must be transient and reversible allowing the ligand to dissociate from one soluble receptor and become available for binding to another soluble receptor or to a membrane receptor from which it would dissociate more slowly. Experiments were carried out to determine if the protein of the invention exhibited the same property and thus delay rather than inhibit IL-TIF/IL-22 action.

It was found that the effect of IL-TIF/IL-22 on STAT-activation in HT-29 cells reached its peak after 4-6 hours, and decreased dramatically at 24 hours but the receptor of the invention had the same inhibitory effect throughout the assay, indicating that it could not delay IL-TIF/IL-22 activity in vitro.

EXAMPLE 8

Example 2, supra, referred to the identification of a second band in some tissue samples. The band was excised, and sequenced using an automated, fluorescence based system, and art recognized methods. The sequence, set forth at SEQ ID NO. 10, includes an additional 96 nucleotides, corresponding to 32 additional amino acids in the predicted protein (SEQ ID NO. 11).

The preceding examples disclose the aspects of this invention, including isolated nucleic acid molecules which encode a soluble, receptor-like antagonist of IL-TIF/IL-22 such as those with the amino acid sequence of the protein encoded by the nucleotide sequences set forth in SEQ ID NO: 5 or 10. It will be appreciated by one of ordinary skill that the degeneracy of the genetic code facilitates the preparation of nucleic acid molecules which may not be identical to the nucleotide sequence of SEQ ID NO: 5 or 10, but which encode the same protein. Of course, SEQ ID NO: 5 or 10 are preferred embodiments of this invention, but other embodiments are also a part of the invention. Genomic DNA, complementary DNA, and RNA, such as messenger RNA, are all to be included therein. Isolated nucleic acid molecules from other animal species, including other mammals, are also a part of the invention. A preferred aspect of the invention are isolated nucleic acid molecules whose complements hybridize to SEQ ID NO: 5 or 10 under stringent conditions. "Stringent conditions," as used herein, refer, for example, to hybridization at 65° C. in buffer (3.5×SSC), 0.02% Ficoll, 0.02% polyvinylpyrrolidone, 0.02% bovine serum albumin, 25 mM $NaH_2PO_4$ (pH 7), 0.1% SDS, 2 mM EDTA, followed by a final wash at 2×SSC, room temperature and then 0.1×SSC/0.2×SDS at temperatures as high as, e.g., about 65° C. More stringent conditions, such as 0.1×SSC, can also be used. These nucleic acid molecules encode proteins, such as those with amino acid sequences set forth at SEQ ID NO: 6 or 11. The soluble, receptor-like antagonist of this invention may be found in glycosylated or non-glycosylated, sulfated and non-sulfated forms and so forth. Also a part of the invention are isolated nucleic acid molecules which encode proteins having at least 30%, preferably at least 45%, more preferably at least 60%, and most preferably 90% amino acid identity with an amino acid sequence of a protein encoded by SEQ ID NO: 5 or 10.

Also a part of the invention are expression vectors which include the nucleic acid molecules of the invention, operably linked to a promoter, so as to facilitate expression of the DNA. It is well within the skill of the artisan to prepare such vectors.

The vectors, as well as the nucleic acid molecules per se, can be used to prepare recombinant cells, such as isolated recombinant cells, be these eukaryotic or prokaryotic, wherein either an expression vector or the nucleic acid molecule itself is incorporated therein. E. coli cells, COS cells, CHO cells, Sf9 cells etc., are all examples of types of cells which may be used in accordance with this aspect of the invention.

Proteins encoded by the above referenced nucleic acid molecules, preferably in isolated form, are another feature of this invention. By "protein" is meant both the immediate product of expression of the nucleic acid molecules, glycosylated forms of it, forms of the molecule following peptide signal cleavage, such as mature and/or processed forms of the protein, as well as multimeric forms, such as dimers, trimers, and so forth. Also a part of the invention are multimers, such as dimers, which contain at least one protein molecule of the invention, and at least one, different protein molecule. These multimers may be homomeric or heteromeric, such as heteromeric forms that include at least one molecule of a different soluble receptor, a transmembrane receptor, and so forth. Such multimers may bind only a single specific ligand. Also a part of the invention are complexes of the IL-22BP and a ligand, which then act as heteromeric cytokines in transmembrane receptors. Such structures parallel, e.g., the structure of IL-12. Also a feature of this invention is a protein consisting of the amino acid sequence set forth in SEQ ID NO: 6 or 11. Also included as a feature of this invention are proteins that are essentially identical to the sequence in SEQ ID NO: 6 or 11 having only conservative amino acid substitutions. Also included as a feature of the inventions are constructs, such as fusion proteins, where all or a part of the proteins described supra are linked in some fashion, e.g., to a "fusion partner, which is" at least one additional protein or peptide, or amino acid sequence. The "fusion partner" may be, for example, a molecule which provides a recognizable signal, either directly or indirectly, such as a FLAG peptide, β-galactosidase, luciferase, an Fc immunoglobulin, a fluorescent protein, such as "GFP" (green fluorescent protein), and so forth. These fusion partners are preferably joined to the molecule which is described supra at the N- and/or C-terminus of the protein; however, it is to be understood that there are many techniques known for joining molecules to amino acids, and any and all of these methodologies can produce constructs which are a part of the invention.

The individual protein molecules of the invention will preferably have a molecular weight of from about 23 to about 40 kilodaltons as determined by SDS-PAGE. In multimeric forms, the molecular weight of the complex will, of course, vary, but the individual molecules contained therein will each have a molecular weight of about 23-40 kilodaltons, as determined by SDS-PAGE. These molecular weights, it is to be understood, refer to monomeric proteins. Glycosylated monomers will have higher molecular weights, e.g., up to at least about 40-50 kilodaltons.

The proteins preferably consist of at least about 180 and no more than about 300 amino acids. More preferably, the protein consists of about 230-275, more preferably 230-268, most preferably 231-263 amino acids. Preferably, the amino acids sequences consists of or comprises all or part of the amino acid sequences encoded by SEQ ID NO: 6 or 11. Such binding proteins can be produced via, e.g., transforming host cells with one or more nucleic acid molecules or expression vectors in accordance with the invention, culturing the transformant, and then isolating the resulting, recombinant binding protein.

It will be appreciated by the skilled artisan that the proteins encoded by the above recited nucleic acid molecules are a feature of the invention, and may be used to produce antibodies, in accordance with standard protocols. Such antibodies, in monoclonal and polyclonal form, constitute a further feature of the invention as do fragments of said antibodies, chimeric forms, humanized forms, recombinant forms, hybridoma cell lines which produce the antibodies and so forth. Also a feature of the invention are immunogens, comprising all or a part of the amino acid sequence of protein molecules of the invention, preferably combined with an adjuvant, such as Complete or Incomplete Freund's Adjuvant. Portions of the protein sequences may be linked to other molecules, such as keyhole limpet hemocyanin, to render them more immunogenic. These antibodies can be used, e.g., to determine if the proteins of the invention are present. This is a further feature of the invention, as is now explained.

It has been shown, in the examples, that the nucleic acid molecules of the invention encode proteins that block IL-TIF/IL-22 activity. Hence, a further feature of the invention is a method inhibiting IL-TIF/IL-22 activity, such as the activation of STAT transcription factors and acute phase reactant production by contacting a sample with an amount of the protein of this invention sufficient to inhibit or block the activity of IL-TIF/IL-22.

One could also use these molecules to test the efficacy of IL-9 agonists or antagonists when administered to a subject, such as a subject suffering from lymphoma, an immune system disorder such as an allergy, acquired immune deficiency syndrome, autoimmune diabetes, thyroiditis, or any of the other conditions described in, e.g, U.S. Pat. Nos. 5,830,454; 5,824,551, and pending application Ser. No. 08/925,348, filed on Sep. 8, 1997 now allowed, all of which are incorporated by reference. The molecules can also be used to modulate the role of IL-9 in these and other conditions. To elaborate, since IL-9 induces IL-TIF/IL-22 and the proteins of this invention block the activity of IL-TIF/IL-22, the proteins of this invention are useful as IL-9 activity modulators. Thus, a further aspect of the invention is a method to determine activity of endogenous IL-9, such as in situations where excess IL-9 activity is implicated, including asthma, allergies, and lymphomas. One can also block or inhibit IL-9 activity by blocking or inhibiting IL-TIF/IL-22 or IL-TIF/IL-22 activity, using the receptor-like antagonist of this invention. Examples of conditions which can be treated by the use of the protein of this invention are allergies, asthma, lymphoma, and so forth. The ability to regulate IL-9 activity is important in conditions such as those listed supra, as well as conditions such as apoptosis, including cortisol induced apoptosis, conditions involving the nuclear expression of BCL-3, since IL-9 is known to induce such expression, and so forth.

IL-TIF/IL-22 type molecules may either promote regeneration or inhibit differentiation of tissue types in which these molecules are active. IL-TIF/IL-22 molecules target various cancer and normal cell lines (i.e., mesangial and neuronal cells, as well as melanoma and hepatoma cells. See, e.g., U.S. patent application Ser. No. 09/626,617 filed incorporated by reference). Hence, another feature of the invention is a method of treatment of a patient in need thereof wherein the proteins of this invention are used to inhibit the activity of IL-TIF/IL-22, in, e.g., neoplastic tissue, such as melanoma or hepatoma.

It will be clear to the skilled artisan that IL-TIF/IL-22 can regulate the inflammatory response. A preferred aspect of this regulation is the modulation of the acute phase response by organs, such as the liver, by administering the receptor-like antagonist of this invention. See, e.g., Janeway et al., *Immunobiology*, ($4^{th}$ edition), incorporated by reference. Janeway explains that various cytokines such as IL-1, IL-6 and TNF-α activate hepatocytes to synthesize acute phase proteins, such as c-reactive protein, and mannan binding lectin, as well as those described in the examples, supra.

IL-TIF/IL-22 has a role in activating acute phase proteins. Thus another aspect of this invention is a method for reducing the production of acute phase proteins, stimulated by IL-10 TIF/IL-22, by administering an amount of the receptor-like antagonist of this invention to a tissue sample or to a patient in need thereof, wherein said amount is sufficient to reduce production or activity of acute phase proteins.

Also a part of the invention are methods for regulating activity of IL-TIF/IL-22 by administering the receptor-like antagonist to regulate IL-TIF/IL-22 activity. Also a part of this invention is a method for determining the presence of the receptor-like antagonist of this invention in a tissue or cell sample comprising contacting said sample with an antibody specific for said receptor-like antagonist and determining binding therebetween. Methods for determining the binding of an antibody and its antigen are well known to those of skill in the art and need not be elaborated herein.

The receptor-like antagonist of this invention may also be used to determine the presence of IL-TIF/IL-22 in a sample by, e.g., labeling said receptor-like antagonist and then contacting said sample with said receptor-like antagonist and determining binding therebetween wherein said binding is indicative of the presence of IL-TIF. Alternatively, one may determine the presence of IL-TIF/IL-22 in a sample by treating a cell line that is responsive to IL-TIF/IL-22 to two aliquots of said sample, one containing the receptor-like antagonist and one without the receptor-like antagonist, then measuring and comparing the response of said responsive cell to the two aliquots wherein a difference in response to the two aliquots is indicative of the presence of IL-TIF/IL-22. In the alternative, cells that are responsive to IL-TIF/IL-22 can be used in such assays. To elaborate, cells which show some type of response to IL-TIF/IL-22, such as increased STAT activation or acute phase reactant production, can be used to screen for presence and/or amount of IL-22BP in a sample. For example, assuming that the cell is incubated in the sample in question together with ILTIF/IL-22, any observed change in the response, such as a decrease in STAT activation or acute phase reactant production, is indicative of IL-22 BP in said sample.

The soluble IL-TIF/IL-22 binding proteins described herein are further examples of soluble, cytokine receptors generated in vivo. See, e.g. Rose-John, et al., Biochem J. 300: 281 (1994); Femandez-Botran, et al., Adv. Immunol 63:269 (1996). Heaney, et al., Blood 87: 845 (1996). Soluble cytokine receptors compete with cell surface receptors for binding to free or unbound cytokine molecules. With the exception of IL-6R, this binding prevents cytokines from reaching the cell membrane and generating a signal. The binding is generally reversible, leading to temporary sequestration of the cytokine from membrane receptors. Soluble cytokine receptors also enhance the activity of cytokines by modifying their stability, decreasing proteolytic degradation, or reducing clearance. Such functions, i.e., as cytokine carriers in vivo, are seen to help potentiate the systemic effect of cytokines, with the antagonistic effect being pertinent to paracrine activities.

Other features of the invention will be clear to the artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which encodes a soluble protein which binds to IL-TIF/IL-22 comprising the nucleotide aequence of SEQ ID NO: 5.

2. An isolated nucLeic acid molecule which encodes a soluble protein which binds to IL-TIF/IL-22, consisting of the nucleotide sequence set forth at SEQ ID NO: 5.

* * * * *

UNITED STATES PATENT AND TRADEMARK OFFICE
CERTIFICATE OF CORRECTION

PATENT NO. : 7,268,223 B2 Page 1 of 1
APPLICATION NO. : 09/919162
DATED : September 11, 2007
INVENTOR(S) : Jean-Christophe Renauld and Laure Dumoutier It is certified that error appears in the above-identified patent and that said Letters Patent is hereby corrected as shown below:

Column 19: in claim 1, line 3, "aequence" should read --sequence--.

Column 20: in claim 2, line 1, "nucLeic" should read --nucleic--.

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,268,223 B2  Page 1 of 1
APPLICATION NO. : 09/919162
DATED : September 11, 2007
INVENTOR(S) : Renauld et al.

It is certified that error appears in the above-identified patent and that said Letters Patent is hereby corrected as shown below:

On the cover page, item

[*] Notice:   Subject to any disclaimer, the term of this patent is extended or adjusted under 35 USC 154(b) by 444 days Delete the phrase "by 444 days" and insert -- by 329 days --

Signed and Sealed this

Twenty-fourth Day of February, 2009

JOHN DOLL
*Acting Director of the United States Patent and Trademark Office*